United States Patent [19]

Feier et al.

[11] Patent Number: 4,580,093

[45] Date of Patent: Apr. 1, 1986

[54] METHOD AND APPARATUS FOR CORRECTING COINCIDENCE ERRORS DURING COUNTING OF TWO TYPES OF PARTICLES

[75] Inventors: Markus Feier, Otelfingen; Ulrich Marti, Bachenbülach, both of Switzerland

[73] Assignee: Contraves AG, Zürich, Switzerland

[21] Appl. No.: 517,255

[22] Filed: Jul. 25, 1983

[30] Foreign Application Priority Data

Aug. 17, 1982 [CH] Switzerland .................. 4918/82

[51] Int. Cl.[4] ................ G01N 27/00; G06M 11/04
[52] U.S. Cl. ................................. 324/71.4; 377/11
[58] Field of Search ............. 324/71.4, 71.1; 377/10, 377/11, 12; 364/555

[56] References Cited

U.S. PATENT DOCUMENTS

| | | | |
|---|---|---|---|
| 3,936,741 | 2/1976 | Coulter | 324/71 LP |
| 3,938,038 | 2/1976 | Campbell | 377/50 |
| 3,940,691 | 2/1976 | Hogg | 324/71 LP |
| 4,009,443 | 2/1977 | Coulter et al. | 328/111 |
| 4,447,883 | 5/1984 | Farrell | 324/71.4 |

FOREIGN PATENT DOCUMENTS 2022878  5/1970  Fed. Rep. of Germany .
2449321  4/1975  Fed. Rep. of Germany .
3020263  4/1980  Fed. Rep. of Germany .
2399656 11/1978  France .

*Primary Examiner*—Stewart J. Levy
*Assistant Examiner*—Robert R. Raevis
*Attorney, Agent, or Firm*—Werner W. Kleeman

[57] ABSTRACT

During a predetermined measuring time there are generated electrical pulses in a detector arrangement, each of these electrical pulses corresponding to a respective particle which is to be counted. The pulse amplitude of the electrical pulses corresponds to the particle size. In a discriminator circuit the electrical pulses are compared with a threshold value. Those pulses, the pulse amplitude of which exceeds the threshold value, are inputted to a counter circuit and a time measuring circuit for measuring the total time duration of the electrical pulses. All of the electrical pulses are delivered to a further counter circuit and a time measuring circuit. The digital values derived from both counter circuits and both time measuring circuits are infed to a digital computer in which there is computed according to the equation $Z_T{}^* = (Z_S - Z_E) \cdot T_S/(T_S - T_E)$ a count result $Z_T{}^*$ for the pulses, the pulse amplitude of which does not exceed the threshold value. This count result $Z_T{}^*$ has been corrected by the cross-coincidence error.

2 Claims, 1 Drawing Figure

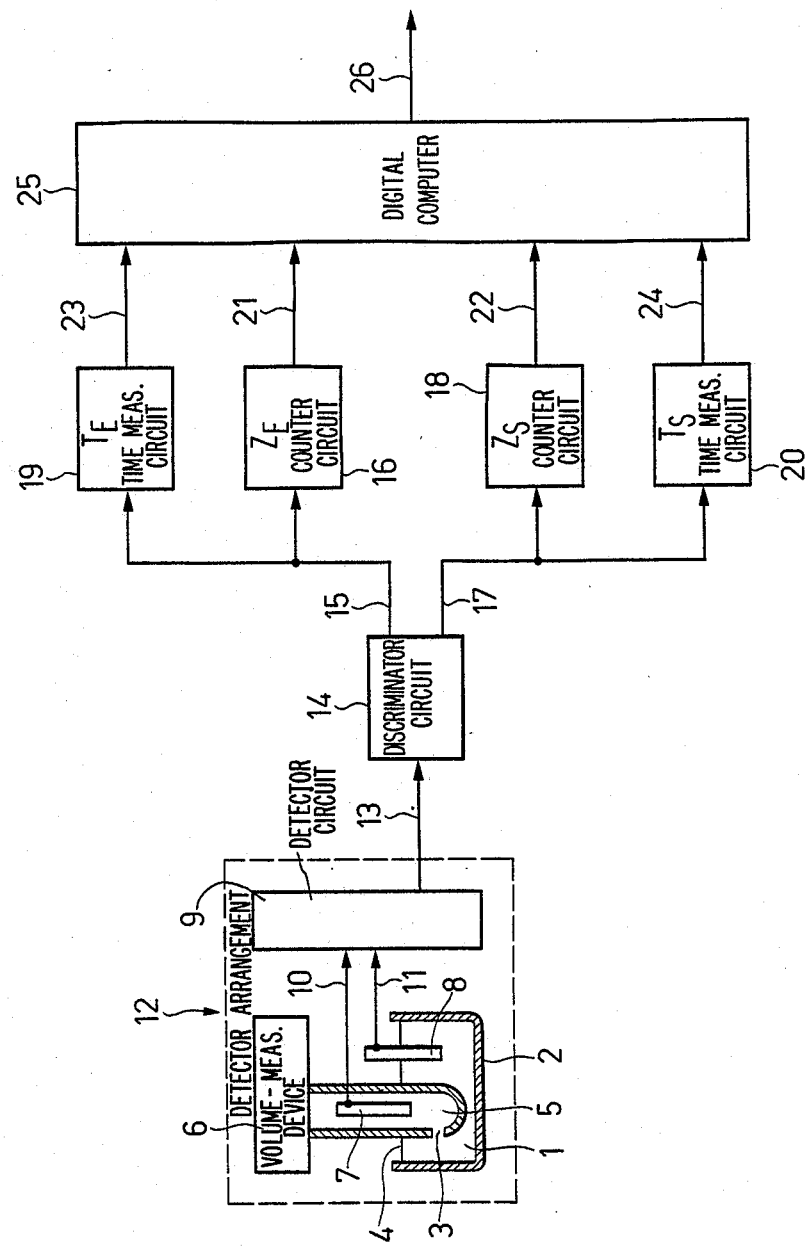

METHOD AND APPARATUS FOR CORRECTING COINCIDENCE ERRORS DURING COUNTING OF TWO TYPES OF PARTICLES

BACKGROUND OF THE INVENTION

The present invention relates to a new and improved method of, and apparatus for, correcting coincidence errors during the counting of two types of particles.

In its more particular aspects, the present invention is concerned with a new and improved method of, and apparatus for, the correction of coincidence errors during the counting of particles of a first type in the presence of particles of a second type in a mixed or hybrid suspension containing both types of particles. The particles of the second type are larger than and present in a higher concentration than the particles of the first type. For instance, the invention is especially concerned with the counting of thrombocytes in a diluted blood sample which contains therein erythrocytes in a much higher concentration than the thrombocytes.

A method and apparatus for counting of thrombocytes in the presence of erythrocytes have been disclosed, for instance, in German Patent Publication No. 3,020,263. According to the teachings of such patent the particles of a diluted blood sample generate electrical pulses in an analyzer, the amplitude of which pulses corresponds to the particle size. The pulse amplitude is compared with a threshold value which is set such that the smaller thrombocyte pulses can be distinguished from the much larger erythrocyte pulses. Both types of pulses are separately counted. The result of the thrombocyte-count is reduced by subtraction of a correction element, in order to correct the error caused by the co-counted erythrocyte particles. The correction element which is to be subtracted is a polynomial function of the result of the erythrocyte-count.

As has been found such type of correction fulfils the purpose of eliminating from the result of the thrombocyte-count the errors caused by the too small erythrocyte pulses. The aforementioned too small erythrocyte pulses, which are falsely counted as thrombocyte pulses, are caused whenever an erythrocyte particle passes through the measuring aperture or opening of the analyzer in an abnormal or irregular manner, for instance extremely slowly or along an extremely eccentric path of travel. The frequency of occurrence of such abnormal or irregular pulses at least approximately corresponds to a polynomial function of the number of erythrocytes or erythrocyte particles, and therefore, it should be readily understood that there must be subtracted from the uncorrected count result the corresponding false counts.

However, with this particle counting method and apparatus there is absolutely not corrected a different type of error which arises, namely the so-called cross-coincidence error which is caused during the simultaneous presence or coincidence of thrombocyte particles with an erythrocyte particle in the measuring aperture or opening. With such type of errors the smaller thrombocyte pulse or pulses are masked by the much larger erythrocyte pulse.

SUMMARY OF THE INVENTION

Hence, with the foregoing in mind it is a primary object of the present invention to overcome the aforementioned drawbacks and shortcomings of the prior art proposals.

Another and more specific object of the present invention is directed to a new and improved particle counting method and apparatus, wherein it is possible to reliably correct such cross-coincidence errors.

A further significant object of the present invention is directed to a new and improved method of, and apparatus for, reliably correcting coincidence or cross-coincidence errors during counting of two types of particles, especially thrombocytes and erythrocytes.

The correction of coincidence errors during the counting of a single type of particle is already known to the art. Thus, in German Patent Publication No. 2,449,321, it is known to count the particle pulses during a predetermined time span and to prolong such time span by a time increment which is a function of the width, amplitude and/or frequency of the pulses. Furthermore, from U.S. Pat. No. 3,938,038, granted Feb. 10, 1976, it is known to count the particle pulses during a predetermined time span and to increase the counting result by multiplication with a factor which is a function of the summated duration of all counted pulses. Both the aforementioned German Patent Publication No. 2,449,321 and U.S. Pat. No. 3,938,038 do not provide any teaching by means of which it is possible to solve the objects of the present invention; during the counting of the previously mentioned mixture of particles the correction function is governed by the width, height, frequency or summated duration of the most frequent and largest pulses, so that the counting of the particles of the first type is falsely corrected by a function of the counting of the particles of the second type.

Therefore, with the foregoing in mind it is also a further important object of the present invention to form the correct or proper correction function for the correction of the cross-coincidence error and to properly modify the count result by means of such correction function.

Now in order to implement these and still further objects of the invention, which will become more readily apparent as the description proceeds, the method of the present development serves for the correction of coincidence errors during the counting of particles of a first type in the presence of particles of a second type in a mixed or hybrid suspension containing both types of particles, wherein the particles of the second type are larger and present in a greater concentration than the particles of the first type, and especially serves for the counting of thrombocytes in the presence of erythrocytes in a diluted blood sample. Electrical pulses are generated, each of which correspond to a respective particle, the pulse amplitude of such electrical pulses corresponding to the particle size. These pulses are generated during a predetermined measuring time and counted. Based upon the pulse amplitude there is distinguished between the first pulses, corresponding to the first type of particles, and the second pulses corresponding to the second type of particle.

In accordance with important aspects of the method of the invention there are specifically accomplished the steps of:

Counting as well as measuring the total time duration of all pulses for forming a count result $Z_S$ and a total time duration $T_S$;

Counting and measuring the total time duration of the second pulses for forming a count result $Z_E$ and a total time duration $T_E$; and Forming a count result $Z_T^*$, corrected in relation to the cross-coincidence error, for the first pulses according to the equation:

$$Z_T^* = (Z_S - Z_E) \cdot \frac{T_S}{(T_S - T_E)}$$

As already alluded to above, the invention is not only concerned with the aforementioned method aspects, but also concerns apparatus for the performance of such method. According to the apparatus aspects of the invention there is provided a detector arrangement for the generation of pulses each corresponding or related to a respective particle, a discriminator circuit for the comparison of the pulse amplitude with a threshold value for distinguishing the first and second pulses from one another, and wherein the pulse amplitude of the second pulses exceeds the threshold value. There are also provided two counter circuits cooperating with the discriminator circuit. Importantly, there are also provided two digital time measuring circuits and a digital computer, the discriminator circuit delivers at one line or conductor thereof all of the pulses in a form suitable for digital counting thereof and at another line or conductor only delivers the second pulses in a form suitable for digital counting thereof. The pulses delivered at the one line are inputted to one of the counter circuits and one of the time measuring circuits and the pulses delivered at the other line are inputted to the other counter circuit and the other time measuring circuit. Both of the counter circuits as well as both of the time measuring circuits are operatively connected at the output side thereof by means of suitable lines or conductors with the digital computer, at the output of which there appears a count result for the first pulses which is corrected by the cross-coincidence error.

BRIEF DESCRIPTION OF THE DRAWING

The invention will be better understood and objects other than those set forth above, will become apparent when consideration is given to the following detailed description thereof. Such description makes reference to the annexed drawing wherein the single FIGURE schematically illustrates in block circuit diagram an exemplary form of apparatus for the performance of the inventive method of counting two different types of particles and for correcting coincidence errors arising during the counting of such particles.

DETAILED DESCRIPTION OF THE PREFERRED EMBODIMENTS

Describing now the drawing, it is to be understood that only enough of the details of the construction of the particle counting and correction apparatus have been conveniently shown in the single FIGURE as needed to enable those skilled in the art to readily understand the underlying principles and concepts of the present development, while simplifying the showing of the drawing. Also, in order to simplify the explanation and to provide a reference point for understanding the following disclosure of the invention, it will be understood that in the description to follow there will be considered the case where the particles of the first type constitute thrombocytes and the particles of the second type constitute erythrocytes. Equally, for simplification purposes the corresponding pulses have been conveniently referred to herein as "thrombocyte pulses" and "erythrocyte pulses".

In a manner well known in this technology, for instance as disclosed in the aforementioned German Patent Publication No. 3,020,263, the thrombocyte pulses and the erythrocyte pulses are differentiated from one another and counted during a predetermined measuring time. Equally, in a manner known, for instance, from the likewise aforementioned German Patent Publication No. 2,449,321, there is measured the duration of each pulse, in other words, there is determined the length of time during which the pulse amplitude exceeds a threshold value. Additionally, this pulse duration of the corresponding type of pulse is correlated either to a thrombocyte pulse or an erythrocyte pulse. During the measuring or measurement time there is added-up, on the one hand, the duration of the thrombocyte pulses, and, on the other hand, the duration of the erythrocyte pulses (for simplification there are here ignored spurious pulses which, for instance, could be caused by leukocytes or cell fragments). Thus, there is formed a total time duration $T_T$ of the thrombocyte pulses and a total time duration $T_E$ of the erythrocyte pulses; as needed, there can be computed therefrom also a total time duration $T_S = T_T + T_E$ of all pulses.

Starting from the consideration that there is not detected any thrombocyte pulse during such time that there appears an erythrocyte pulse, in other words, that the time during which there are available erythrocyte pulses functions as dead time of the detection apparatus for the detection of the thrombocyte pulses, it is necessary to compensate the measuring time by the dead time in order to correct the cross-coincidence error. For this purpose the count result $Z_T$ of the thrombocyte pulses, detected during the predetermined measuring time, are related to the dropped-out measuring time, that is to say, to the measuring time corrected by the dead time. This can be expressed by the following equation (1):

$$Z_T^* = Z_T \cdot \frac{(T_T + T_E)}{T_T} \tag{1}$$

wherein, $Z_T$ represents the uncorrected and $Z_T^*$ the corrected count result of the thrombocyte pulses.

In terms of the principles of the invention and the obtained results it is equivalent, although capable of accomplishment with much simpler apparatus, to detect and sum-up, on the one hand, the erythrocyte pulses and their duration, and, on the other hand, all pulses and their duration. In such case the count result $Z_T$ of the thrombocyte pulses results as the difference of the count result $Z_S$ for all pulses and the count result $Z_E$ for the erythrocyte pulses, and the total time duration $T_T$ of the thrombocyte pulses appears as the difference of the total time duration $T_S$ of all pulses and the total time duration $T_E$ of the erythrocyte pulses, that is to say, $Z_T = (Z_S - Z_E)$ and $T_T = (T_S - T_E)$. Under these circumstances there results the corrected count result of the thrombocyte pulses from the following equation (2):

$$Z_T = (Z_S - Z_E) \cdot \frac{T_S}{(T_S - T_E)} \tag{2}$$

With the benefit of the foregoing detailed explanation of the method of the present invention there will now be considered with respect to the single FIGURE of the drawing an exemplary embodiment of apparatus for the performance of such method. This block circuit diagram depicts in block schematic form individual elements of the inventive apparatus which basically are well known as such in the art, and therefore need not here be disclosed in any greater detail beyond the discussion given hereinafter concerning such individual electronic components. Reference is made in this regard in particular to the previously mentioned German Patent Publication No. 3,020,263 and German Patent Publication No. 2,449,321. Furthermore, it will be understood that a suspension 1 containing the previously mentioned mixture of particles, for instance a diluted blood sample, is held in a vessel or container 2. This suspension 1 of the diluted blood sample is sucked-up into a measuring chamber 5 through a small measuring opening or aperture 3 which is located below the liquid level or meniscus 4 of the suspension 1. The quantity of the sucked-up suspension 1 is determined by a suitable volume-measuring device 6. The time needed for the sucking-up of the blood sample constitutes the previously mentioned predetermined measuring time.

Blood particles, which pass through the measuring opening or aperture 3 during such time of sucking-up of the blood sample, cause a change in the electrical impedance at the region of the measuring opening or aperture 3. This impedance change is detected by electrodes 7 and 8 and converted by a detector circuit 9 into electrical pulses. For this purpose, the electrodes 7 and 8 are electrically connected in circuit with the detector circuit 9 by means of the electrical lines or conductors 10 and 11, respectively. The arrangement composed of the elements 1 to 11 may be assumed to collectively form a detector arrangement, generally indicated by reference character 12.

For purposes of simplifying the disclosure of the invention, it is again assumed that the suspension is a diluted blood sample and that it only contains thrombocytes and erythrocytes. In other words, it is assumed that spurious effects, for instance, those which could be caused by leukocytes or cell fragments, are negligible.

During each passage of a particle through the measuring opening or aperture 3 the detector arrangement 12 generates at its output line or conductor 13 a pulse which is inputted to a discriminator circuit 14. By comparing the pulse amplitude with a threshold value or threshold there is determined in the discriminator circuit 14 which pulses have exceeded the threshold value, and thus, should be correlated to an erythrocyte particle or erythrocyte. These erythrocyte pulses are brought by the discriminator circuit 14 into a pulse shape or form which is suitable for accomplishing a faultless count and then are inputted by means of a line or conductor 15 to a counter circuit or counter 16. Additionally, in the discriminator circuit 14 all of the pulses which are furnished by the detector arrangement 12 are brought into a pulse shape or form suitable for the faultless counting thereof, and then such are inputted by means of a line or conductor 17 to a counter circuit or counter 18. A branch of the line 15 conducts the erythrocyte pulses to a time measuring circuit 19 where there is measured the total time duration during which the pulses appear at the line or conductor 15. The time measuring circuit 19 may be constituted, for instance, by a suitable counter to which there are inputted the particle pulses as well as the time pulses of a time pulse generator (clock) by means of an AND-gate or circuit, so that there are counted the time pulses which arrive during such time that there appears a particle pulse, and thus, there is formed in the time measuring circuit 19 a counter state or value corresponding to the total time duration of the present erythrocyte pulses.

In comparable fashion a branch of the line or conductor 17 inputs all pulses to a time measuring circuit 20 where there is measured the total time duration during which there appear at the line or conductor 17 the particle pulses. It should be apparent that, and as has been indicated in the drawing, there are formed in the elements or circuits 16, 18, 19 and 20 as the momentary counter states the digital values $Z_E$, $Z_S$, $T_E$ and $T_S$. These digital values are then delivered by means of respective lines or conductors 21, 22, 23 and 24, suitable for the transmission of digital values in the form of digital signals, to a digital computer 25 where there is appropriately accomplished the computation of the corrected count result of the thrombocyte pulses according to the aforementioned Equation (2). The corrected count result $Z_T^*$ as well as other values, which, as the situation requires, are computed or simply further transmitted, appear at a suitable output line or conductor 26 of the digital computer 25.

While there are shown and described present preferred embodiments of the invention, it is to be distinctly understood that the invention is not limited thereto, but may be otherwise variously embodied and practiced within the scope of the following claims. Accordingly,

What we claim is:

1. In a method for the correction of cross-coincidence errors during counting of particles of a first type in the presence of particles of a second type in a mixed suspension containing both types of particles, wherein the particles of the second type are larger than and present in a higher concentration than the particles of the first type, especially during the counting of thrombocytes in the presence of erythrocytes in a diluted blood sample, wherein there are generated electrical pulses, each of which corresponds to a respective particle, and the pulse amplitude of which corresponds to the particle size, and these pulses are generated and counted during a predetermined measuring time, and wherein based upon the pulse amplitude there is differentiated between first pulses, corresponding to the first type of particles, and second pulses corresponding to the second type of particles, the improvement comprising the steps of:

counting and measuring the total time duration of all pulses;

developing from such counting and measuring of the total time duration of all pulses a count result $Z_S$ and a total time duration $T_S$;

counting and measuring the total time duration of the second pulses;

developing from the counting and measuring of the total time duration of the second pulses a count result $Z_E$ and a total time duration $T_E$; and forming a count result $Z_T^*$, corrected in relation to the cross-coincidence error, for the first pulses according to the equation:

$$Z_T^* = (Z_S - Z_E) \cdot \frac{T_S}{(T_S - T_E)}$$

2. An apparatus for correcting cross-coincidence errors during the counting of particles of a first type in the presence of particles of a second type in a mixed suspension containing both types of particles, the particles of the second type being larger than and present in a greater concentration than the particles of the first type, each particle generating an electrical pulse, the pulse amplitude of which corresponds to the particle size, and such pulses are generated and counted during a predetermined measuring time, and wherein based upon the pulse amplitude there is distinguished between first pulses corresponding to the first type of particles and second pulses corresponding to the second type of particles, comprising:

- a detector arrangement having an output side and serving for generating electrical pulses, each of the electrical pulses corresponding to one of the particles;
- a discriminator circuit operatively connected with said output side of said detector arrangement for comparison of the pulse amplitudes of the electrical pulses with a threshold value for the purpose of distinguishing the first and second electrical pulses from one another, and wherein the pulse amplitude of the second pulses exceeds the threshold value;
- said discriminator circuit having an output side;
- two counter circuits operatively connected with said output side of said discriminator circuit;
- two digital time measuring circuits operatively connected with said output side of said discriminator circuit;
- digital computer means cooperating with said counter circuits and said digital time measuring circuits;
- said discriminator circuit containing at its output side a first line for delivering all electrical pulses in a form suitable for digital counting;
- said discriminator circuit containing at its output side a second line for delivering only the second electrical pulses in a form suitable for digital counting;
- the electrical pulses appearing at said first line being inputted to one of said counter circuits and one of said time measuring circuits;
- the electrical pulses appearing at the second line being inputted to the other counter circuit and the other time measuring circuit;
- each of said counter circuits and time measuring circuit having a respective output side;
- both counter circuits and both time measuring circuits being connected at said output sides thereof by lines with said digital computer; and
- said digital computer having an output side at which there appears a count result for the first pulse which is corrected by the cross-coincidence error.

* * * * *